United States Patent
Tsuta

(10) Patent No.: US 8,020,996 B2
(45) Date of Patent: Sep. 20, 2011

(54) METHOD OF KINETIC PERIMETER

(75) Inventor: Tomohiro Tsuta, Kobe (JP)

(73) Assignee: Tomohiro Tsuta, Kobe (JP)

( * ) Notice: Subject to any disclaimer, the term of this patent is extended or adjusted under 35 U.S.C. 154(b) by 0 days.

(21) Appl. No.: 12/737,729

(22) PCT Filed: Aug. 25, 2009

(86) PCT No.: PCT/JP2009/064803
§ 371 (c)(1),
(2), (4) Date: Feb. 11, 2011

(87) PCT Pub. No.: WO2010/032592
PCT Pub. Date: Mar. 25, 2010

(65) Prior Publication Data
US 2011/0176112 A1    Jul. 21, 2011

(30) Foreign Application Priority Data
Sep. 16, 2008 (JP) .................................. 2008-235935

(51) Int. Cl.
*A61B 3/02* (2006.01)
*A61B 3/00* (2006.01)
(52) U.S. Cl. ....................................... 351/224; 351/246
(58) Field of Classification Search ........... 351/200–246
See application file for complete search history.

(56) References Cited

U.S. PATENT DOCUMENTS

| 4,260,227 | A | * | 4/1981 | Munnerlyn et al. | .......... 351/226 |
| 6,726,327 | B2 | * | 4/2004 | Torrey et al. | .................. 351/243 |

FOREIGN PATENT DOCUMENTS

| JP | S58-121937 | 7/1983 |
| JP | H4-135534 | 5/1992 |
| JP | H14-306413 | 10/2002 |
| JP | H16-73545 | 3/2004 |
| JP | H20-36297 | 8/2006 |
| JP | H19-020877 | 2/2007 |
| JP | H19-29112 | 2/2007 |
| JP | H19-75350 | 3/2007 |
| WO | WO2006/106877 | 10/2006 |

\* cited by examiner

*Primary Examiner* — Mohammed Hasan

(57) ABSTRACT

A method for kinetic perimeter of the present invention including: a step of visual field scanning screen generating means; a step of fixation image scan line setting means; a step of fixation image displaying and controlling means; a step of visual target scan line orthogonally setting means; a step of visual target displaying and controlling means; a step of statically displaying and controlling means; a step of static display position storing means; a step of kinetic display and control starting means; a step of detecting means; a step of detection position storing means; a step of visual field mapping screen generating means; a step of visual field mapping means; a step of under the same fixation image scanning continuation means; and a step of, scanning switching means to the scanning under the next fixation image.

2 Claims, 8 Drawing Sheets

METHOD OF KINETIC PERIMETER

BACKGROUND OF THE INVENTION

The present invention relates to a kinetic perimeter, an operational method of a kinetic perimeter, a program for realizing a kinetic perimeter, and a computer-readable recorded medium.

The following are known as previous perimeters: Goldmann perimeter of 510 model [1945], 940 model [1967]; Tubinger perimeter [1957]; Octopus perimeter [1976]. (see, for example, the nonpatent literature 1.)

The explanation of previous perimeters: Goldmann perimeter is the first brightness perimeter, adopting manual method of simultaneous recording, with 4 to 60 degrees of brightness of the visual target and 6 types of visual angle of the visual target, capable of examining visual field of visual angle, and with adjustability of its background brightness. The shortcoming is that it fails to examine the central region within 5 degrees;

Tubinger perimeter [1957] is the first practical, static perimeter, capable of examining the kinetic visual field and the visual field of color, flicker, and etc., adopting manual method of simultaneous recording, with 80 degrees of brightness of the visual target and 100 degrees of brightness of the fixation image and 5 kinds of color and 6 degrees of background brightness, and capable of examining the central and eccentric vision. Its shortcoming is in the difficulty of controlling the visual target movement, and of adjusting the visual target, fixation image, and background illumination lamp;

Octopus perimeter [1976] is the world's first fully automated, static perimeter.

Nonpatent literature 1: "The latest comprehensive dictionary of medical science", Ishiyaku Publishers Inc., 1987, 1990.

There are some instances where a subject feels burdensome in the task of keeping gazing at the fixation image whose position is unchanged over the lengthy visual field examination of previous perimeters, since it causes visual function adaptation, etc.

The operational aspects of the fixation image display control and the visual target display control by the previous perimeters are very monotonous for subjects.

Since the visual field examinations by previous perimeters are very monotonous, there is the high possibility of erroneous responses made by the subjects due to habituation, etc.

The shapes of scotoma and blind spot detected by previous perimeters are very rough, and there exists the considerable discrepancy between the chart resulted from the visual field examination by a previous perimeter and the real shapes of scotoma and blind spot true to the subject.

It is because of relying on previous perimeters that the early detection of visual defects has been failing.

The aim of the present invention is, therefore, to provide a kinetic perimeter reducing the monotony seen in previous perimeters of the display control aspects of the fixation image and the visual target.

The aim of the present invention is to provide a kinetic perimeter reducing the monotony for subjects seen in the previous examinations of visual field.

The aim of the present invention is also to provide a kinetic perimeter capable of reflecting, in much greater detail, the shapes of scotoma and blind spot true to a subject into the image obtained by the examination.

SUMMARY OF THE INVENTION

To achieve the above aim,

The invention of claim 1 is an operational method for a kinetic perimeter including:

A step of means for generating, on an output device, a visual field scanning screen for scanning a visual field of a subject;

A step of means for setting a fixation image scan line and a fixation image display position, for carrying out the scanning of changing the display position of a fixation image with a predetermined spacing, on the visual field scanning screen that is generated, on the output device, by said step of visual field scanning screen generating means;

A step of means for displaying and controlling a fixation image to be fixated by the subject, during a visual field scanning, at a fixation image display position on the fixation image scan line which is set by said step of fixation image scan line setting means;

A step of means for setting a visual target scan line normal to said fixation image scan line, to scan a visual target on said visual field scanning screen;

A step of means for displaying and scanning said visual target on said visual field scanning screen along the visual target scan line set by said step of visual target scan line orthogonally setting means, in order to scan the visual field;

A step of means, which is included in said step of visual target displaying and controlling means, for statically displaying and controlling said visual target for a predetermined moment on said visual target scan line;

A step of means for storing, on a memory device, a position of said visual target statically displayed and controlled for said predetermined moment by said step of statically displaying and controlling means;

A step of means, which is included in said step of visual target displaying and controlling means, for starting a kinetic scan of said visual target along said visual target scan line after said step of statically displaying and controlling means has displayed and controlled said visual target statically for said predetermined moment;

A step of means for, via an input device, detecting a time when said kinetic scan, started by said step of kinetic display and control starting means, of said visual target has first been perceived by the subject's visual field;

A step of means for storing, on the memory device, a position of said visual target at the time of the detection by said step of detecting means;

A step of means for generating a visual field mapping screen, on an output device, to map and display the subject's visual field;

A step of means for carrying out a visual field mapping on said visual field mapping screen, referring to a position of said visual target stored by said step of static display position storing means and a position of said visual target stored by said step of detection position storing means;

A step of means for stopping, through said step of visual target displaying and controlling means, said kinetic scan of said step of kinetic display and control starting means if the time when said kinetic scan has first been perceived by the subject's visual field is detected by said step of detecting means;

A step of scanning continuation means for, by said step of visual target displaying and controlling means through said step of statically displaying and controlling means, displaying and controlling said visual target statically for said predetermined moment, on said visual target scan line at the position of said visual target stored by said step of detection position storing means, And proceeding from said step of static display position storing means onward as above, And continuing the similar scan, under said fixation image displayed, of said visual target scan line by iterating above procedure along said visual target scan line under the condition of said fixation image being displayed by said step of fixation image displaying and controlling means, in order to continue the next scan of said visual target scan line;

And a step of means for, if the scan, under said fixation image, of said visual target scan line is completed by said step of under the same fixation image scanning continuation means, continuing the similar scan, under a next fixation image being displayed, of said visual target scan line by said step of visual target displaying and controlling means with the next fixation image being said fixation image whose display position is changed, by said step of fixation image displaying and controlling means, to a position with said predetermined spacing, along the fixation image scan line set by said fixation image scan line setting means.

The invention of claim 2 is a computer-readable recorded medium recording a program for causing a computer to realize a function including:

Means for generating, on an output device, a visual field scanning screen for scanning a visual field of a subject;

Means for setting a fixation image scan line and a fixation image display position, for carrying out the scanning of changing the display position of a fixation image with a predetermined spacing, on the visual field scanning screen that is generated, on the output device, by said visual field scanning screen generating means;

Means for displaying and controlling a fixation image to be fixated by the subject, during a visual field scanning, at a fixation image display position on the fixation image scan line which is set by said fixation image scan line setting means;

Means for setting a visual target scan line normal to said fixation image scan line, to scan a visual target on said visual field scanning screen;

Means for displaying and scanning said visual target on said visual field scanning screen along the visual target scan line set by said visual target scan line orthogonally setting means, in order to scan the visual field;

Means, which is included in said visual target displaying and controlling means, for statically displaying and controlling said visual target for a predetermined moment on said visual target scan line;

Means for storing, on a memory device, a position of said visual target statically displayed and controlled for said predetermined moment by said statically displaying and controlling means;

Means, which is included in said visual target displaying and controlling means, for starting a kinetic scan of said visual target along said visual target scan line after said statically displaying and controlling means has displayed and controlled said visual target statically for said predetermined moment;

Means for, via an input device, detecting a time when said kinetic scan, started by said kinetic display and control starting means, of said visual target has first been perceived by the subject's visual field;

Means for storing, on the memory device, a position of said visual target at the time of the detection by said detecting means;

Means for generating a visual field mapping screen, on an output device, to map and display the subject's visual field;

Means for carrying out a visual field mapping on said visual field mapping screen, referring to a position of said visual target stored by said static display position storing means and a position of said visual target stored by said detection position storing means;

Means for stopping, through said visual target displaying and controlling means, said kinetic scan of said kinetic display and control starting means if the time when said kinetic scan has first been perceived by the subject's visual field is detected by said detecting means;

Scanning continuation means for, by said visual target displaying and controlling means through said statically displaying and controlling means, displaying and controlling said visual target statically for said predetermined moment, on said visual target scan line at the position of said visual target stored by said detection position storing means, And proceeding from said static display position storing means onward as above, And continuing the similar scan, under said fixation image displayed, of said visual target scan line by iterating above procedure along said visual target scan line under the condition of said fixation image being displayed by said fixation image displaying and controlling means, in order to continue the next scan of said visual target scan line;

And means for, if the scan, under said fixation image, of said visual target scan line is completed by said under the same fixation image scanning continuation means, continuing the similar scan, under a next fixation image being displayed, of said visual target scan line by said visual target displaying and controlling means with the next fixation image being said fixation image whose display position is changed, by said fixation image displaying and controlling means, to a position with said predetermined spacing, along the fixation image scan line set by said fixation image scan line setting means.

According to the first invention of an operational method for a kinetic perimeter, a visual field mapping image, for example, as shown in FIG. 4 can be obtained based on the data generated from a scanning of a visual field by the operational method for a kinetic perimeter of the present invention. The operational method for a kinetic perimeter of the present invention reduces the monotony of the visual field examination.

According to the second invention of a computer-readable recorded medium recording a program, a visual field mapping image, for example, shown in FIG. 4 can be obtained based on the data generated from a scanning of a visual field by the kinetic perimeter of the present invention that can be realized by carrying out the program for realizing the kinetic perimeter of the present invention, which can be made computer-readable. The kinetic perimeter of the present invention reduces the monotony of the visual field examination.

In FIG. 4, a visual field mapping rectangle is filled with a green whose brightness is increased according to severity of the decline in visual function of the corresponding visual field, by a CPU 501.

In FIG. 4, a scotoma 201, a blind spot 203, a connection of scotoma with blind spot 202, etc. are explicitly shown by a cluster of visual field mapping rectangles of bright greens.

The kinetic perimeter of the present invention can map visual function of the visual field.

The kinetic perimeter of the present invention can map not only the scotoma 201 and blind spot 203, but also portions of visual field where visual function declines 204 and portions of visual field where visual function slightly declines 205.

In FIG. 4, not only the scotoma 201 and blind spot 203 but also visual function of the visual field is mapped.

In a visual field mapping image generated by the kinetic perimeter of the present invention, portions of visual field where visual function declines 204 and portions of visual field where visual function slightly declines 205 can also be analyzed regarding their locations, sizes, shapes, etc., from a cluster of the visual field mapping rectangles filled with greens of moderate brightness.

The kinetic perimeter of the present invention can also map the condition of visual function in the vicinity of a fovea 206 of the visual field.

The fovea 206 having the highest functioning among visual field is represented, in FIG. 4, by a cluster of the visual field mapping rectangles filled with greens of lower brightness.

For the kinetic perimeter of the present invention, the CPU 501 forms a visual field mapping rectangle from data obtained by its scanning of a visual field and carries out an image processing for the visual field mapping rectangle based on the data, through which, in the meanwhile, the CPU 501 can generate a visual field mapping image proper for being called scan of visual field, strongly indicating the retinal structure and so forth.

The kinetic perimeter of the present invention may be embodied by a simple setup without the need for voluminous equipment such as Goldmann perimeter and the like.

The kinetic perimeter of the present invention can examine the central portion within 5 degrees of a visual field.

DETAILED DESCRIPTION OF THE INVENTION

Figure 1:
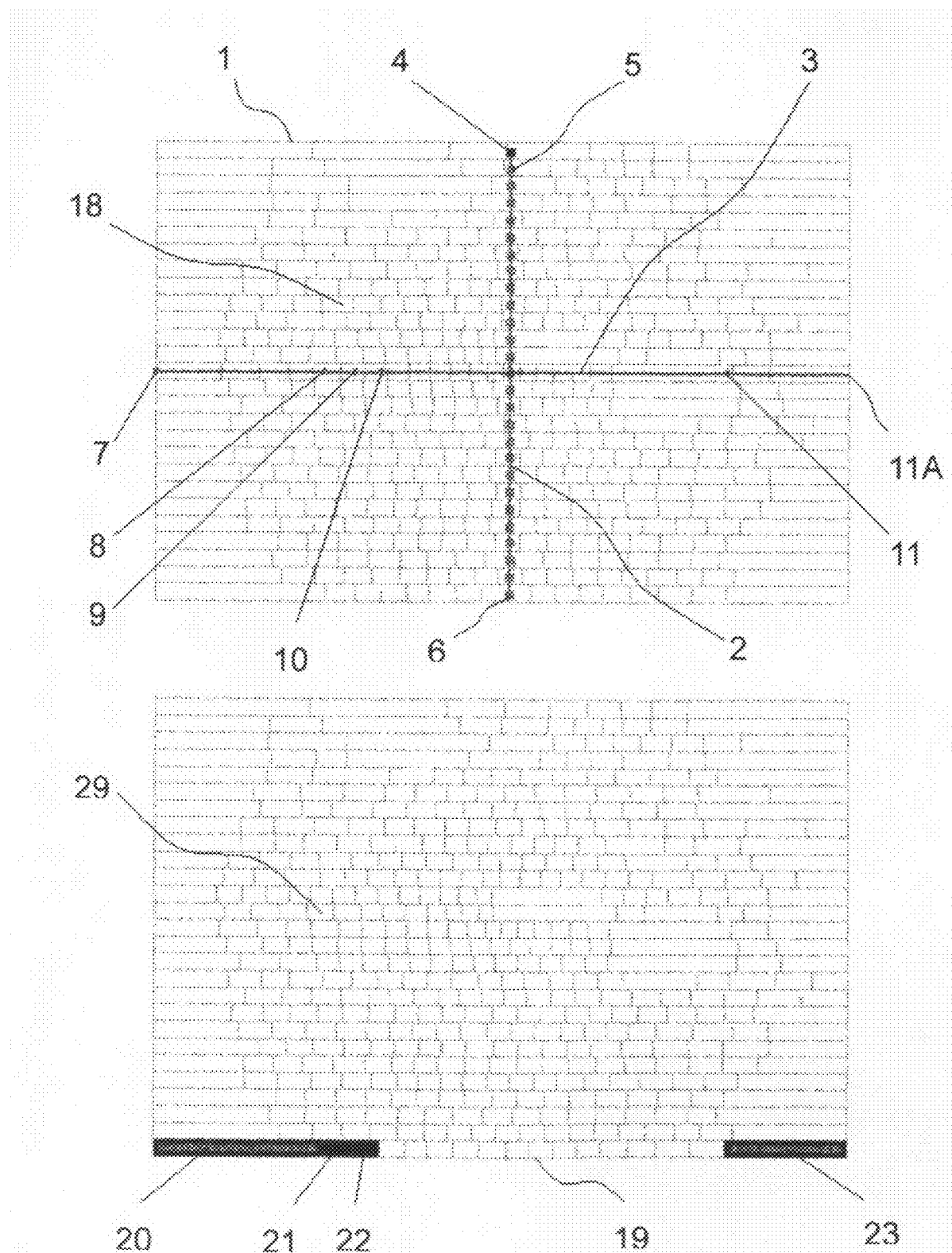
FIG. 1 is a schematic diagram showing a preferred embodiment of the scanning, operation, and visual field mapping aspect of the present invention of the kinetic perimeter.

The detailed explanation of the present invention of a kinetic perimeter, an operational method of a kinetic perimeter, a program for realizing a kinetic perimeter, and a computer-readable recorded medium will be disclosed as below while referring to the drawings.

Figure 5:
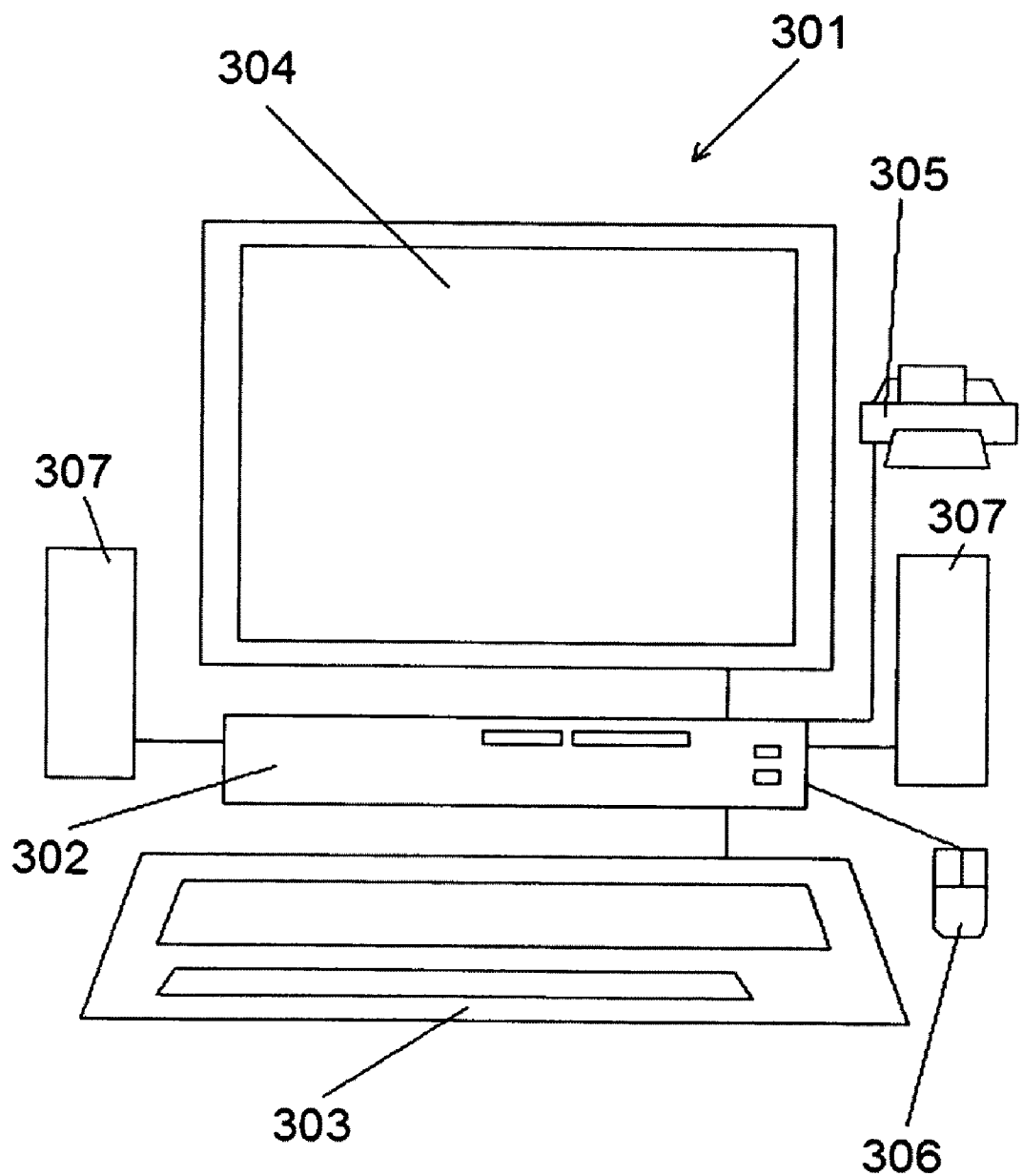
FIG. 5 is a diagram showing a preferred embodiment of the system of the present invention of the kinetic perimeter.
Figure 6:
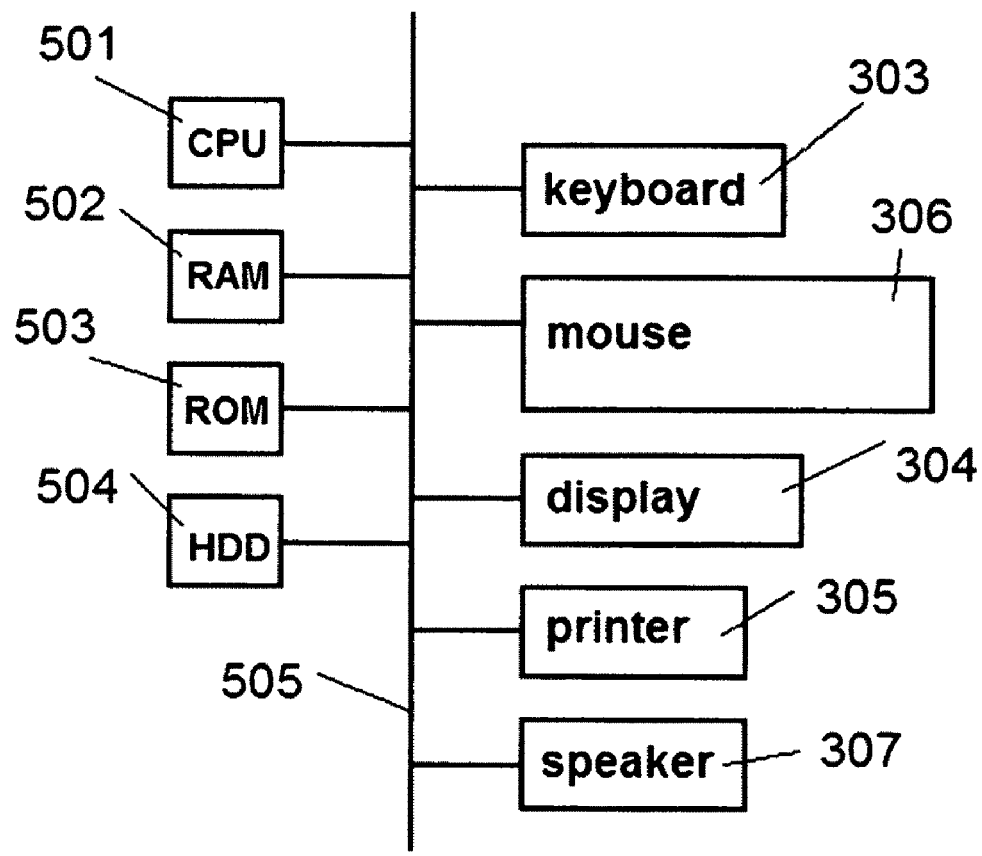
FIG. 6 is a block diagram showing a preferred embodiment of the hardware configuration of the CPU in the present invention of the kinetic perimeter.

Firstly, a setup of the present invention of the perimeter is described referring to FIG. 5 and FIG. 6.

FIG. 5 shows an embodiment of the system of the present invention of the perimeter.

FIG. 6 shows an embodiment of the hardware configuration of the CPU 501 in the present invention of the perimeter.

FIG. 5 shows a computer system 301 diagrammatically.

The present invention of the kinetic perimeter is realized by the computer system 301 carrying out a program for realizing a kinetic perimeter.

As shown in FIG. 5, the computer system 301 realizing an embodiment of the present invention of the kinetic perimeter includes a main unit 302 that is equipped with a CPU (Central Processing Unit) 501, etc., which will be mentioned later, a keyboard 303, (if necessary, a mouse 306), a display 304, and a printer 305 (and if necessary, a speaker 307 too).

Next, an embodiment of the hardware configuration of the CPU 501 in the present invention of the kinetic perimeter is described referring to FIG. 6.

The CPU 501 in the present invention of the kinetic perimeter is configured specifically including:
a microprocessor such as the CPU 501, a RAM (Random Access Memory) 502, a ROM (Read Only Memory) 503, a HDD (Hard Disc Drive) 504, a keyboard 303, a mouse 306, a display 304, a printer 305, a speaker 307, and a communications interface.

These parts are connected via a bus 505.

(The HDD 504 is connected through the input-output interface to the bus 505.)

The keyboard 303 is connected through the input-output interface to the bus 505, which enables output to the CPU 501 of input by the keyboard 303.

The display 304 is connected through the input-output interface to the bus 505, which enables output to the display 304 of image data input from the CPU 501. The printer 305 is connected through the input-output interface to the bus 505, which enables output by the printer 305 of input from the CPU 501.

(The speaker 307 is connected through the input-output interface to the bus 505, which enables output by the speaker 307 of input from the CPU 501.)

(The mouse 306 is connected through the input-output interface to the bus 505, which enables output to the CPU 501 of input through the mouse 306.)

The CPU 501 carries out operations characteristic of an embodiment of the present invention, by loading onto the RAM 502 a program, which is stored in the HDD (Hard Disc Drive) 504, for realizing the present invention of a kinetic perimeter.

The CPU 501 carries out controls, and kinds of arithmetic processing, of the present invention of the kinetic perimeter, according to a program for realizing the present invention of the kinetic perimeter.

The CPU 501 controls display processing of the display 304 (an example of the output device). (Specifically, the CPU 501, for example, displaying and controlling the fixation image and visual target, and generating the visual field mapping image from the data obtained by the present invention of the kinetic perimeter.)

The CPU 501 controls the present invention of the kinetic perimeter according to input by the keyboard 303 (an example of the input device).

The CPU 501 can control the printer 305 and the like so as to output the visual field mapping image, etc. that are generated based on the data obtained from the kinetic perimeter.

(If necessary, the CPU 501 may control the speaker 307 (an example of the output device) to produce output (for example, according to input by an input device such as the keyboard 303 or the like, or, for example, when the display position of a fixation image is changed in the visual field scanning, or, for example, when the visual field mapping image is output, or the like).)

(The CPU 501 may control the present invention of the kinetic perimeter according to input from the mouse 306 (an example of the input device).)

The keyboard 303 (and if necessary, the mouse 306) and the display 304 are used as user interfaces in the present invention of the kinetic perimeter.

The keyboard 303 is used, for example, as a device for input (the input device).

(If necessary, the mouse 306 is used as a device for performing various kinds of operations of input to the display screen of the display 304.)

The display 304 is a display device (the output device), for example, of a LCD (Liquid Crystal Display), a CRT (Cathode Ray Tube), or the like, which scans a visual field in accordance with the present invention of the kinetic perimeter, and displays a visual field mapping image generated by the present invention of the kinetic perimeter.

(If necessary, various screens such as an operation screen and a setting screen may be displayed on the display 304.)

And when the CPU 501 is connected to communications network such as the Internet and a LAN (Local Area Network), the communications interface can be equipped with a network adapter such as a LAN card or communications equipment such as a modem, in order to establish data communication among the network. In such a case, by installing on the network a server storing a program for realizing the present invention of the kinetic perimeter, and configuring the CPU 501 as a client terminal of the server, the operation of the present invention of the kinetic perimeter can be carried out by the perimeter.

A program for realizing the present invention of the kinetic perimeter can be stored on any computer-readable non-transitory media (storage media).

Examples of such non-transitory media (storage media) are an optical disk, a magneto-optic disk (CD-ROM, DVD-RAM, DVD-ROM, MO, etc.), a magnetic-storage device (hard disk, Floppy Disk™, ZIP, etc.), a semiconductor memory, etc.

Next, the detailed explanation regarding the present invention of a kinetic perimeter, operational method of a kinetic perimeter, and program for realizing a kinetic perimeter will be described while referring to FIG. 1, FIG. 2, FIG. 3, FIG. 7 and FIG. 8, as below.

Figure 2:
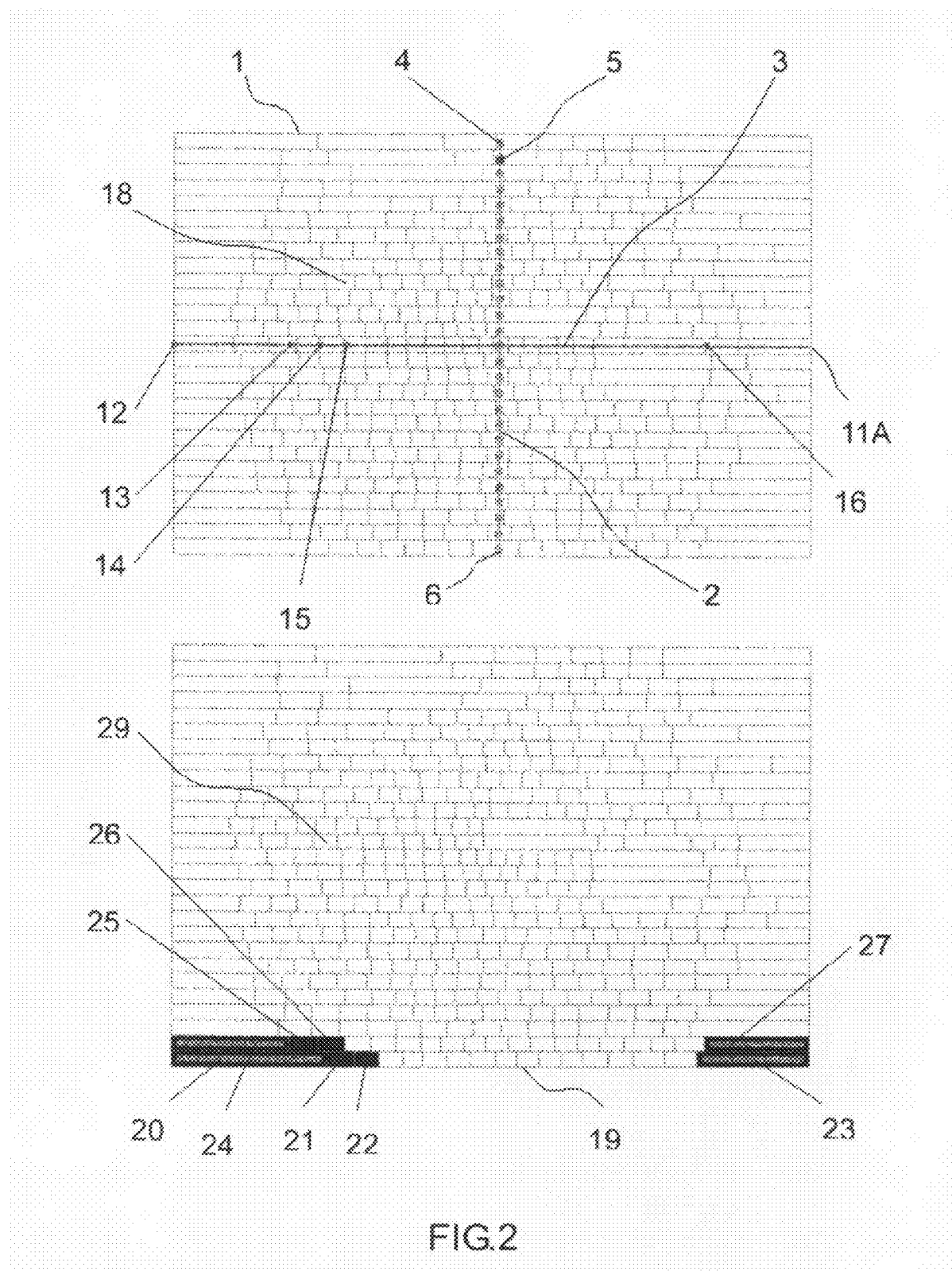
FIG. 2 is a schematic diagram showing a preferred embodiment of the scanning, operation, and visual field mapping aspect of the present invention of the kinetic perimeter.
Figure 3:
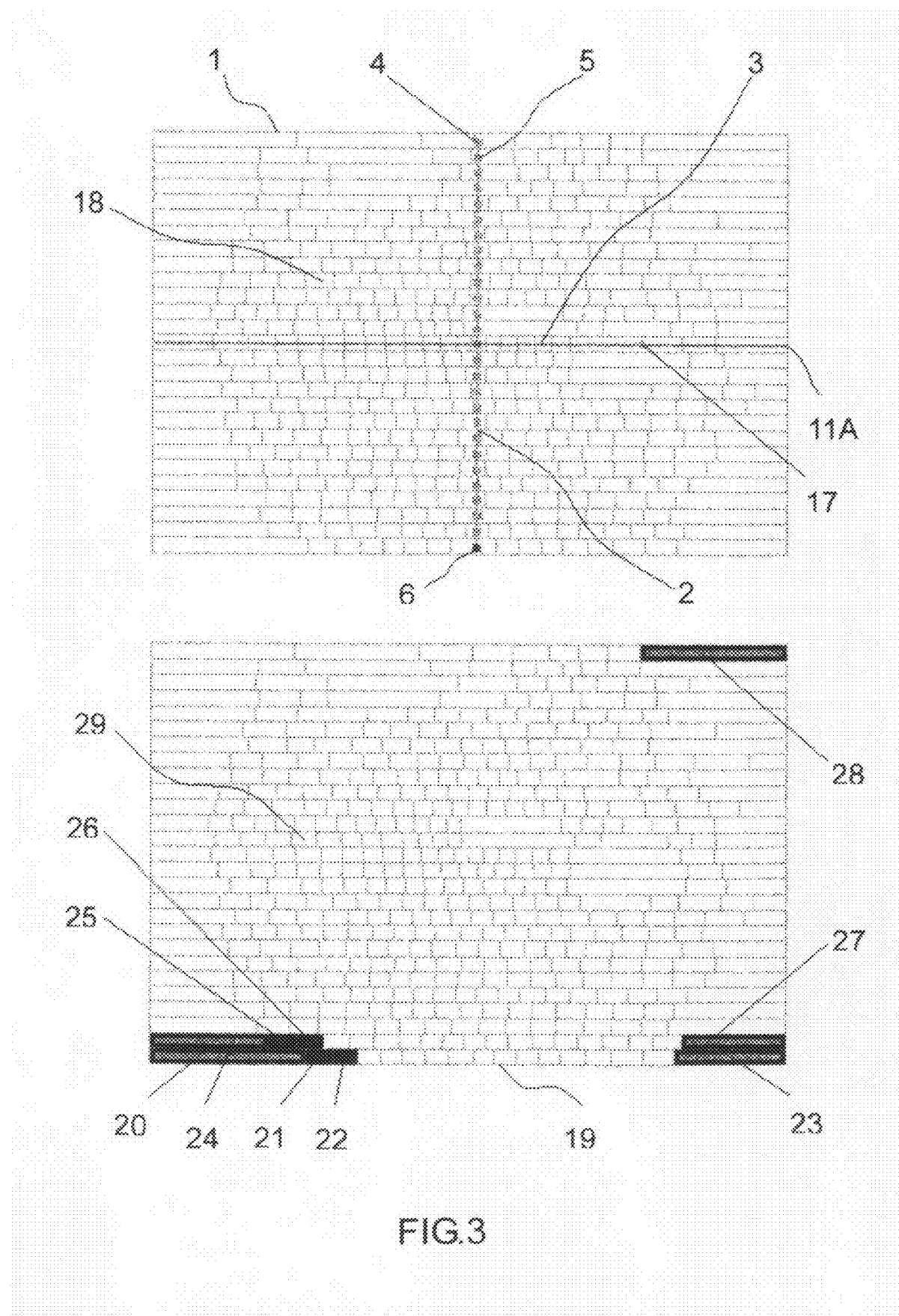
FIG. 3 is a schematic diagram showing a preferred embodiment of the scanning, operation, and visual field mapping aspect of the present invention of the kinetic perimeter.
Figure 4:
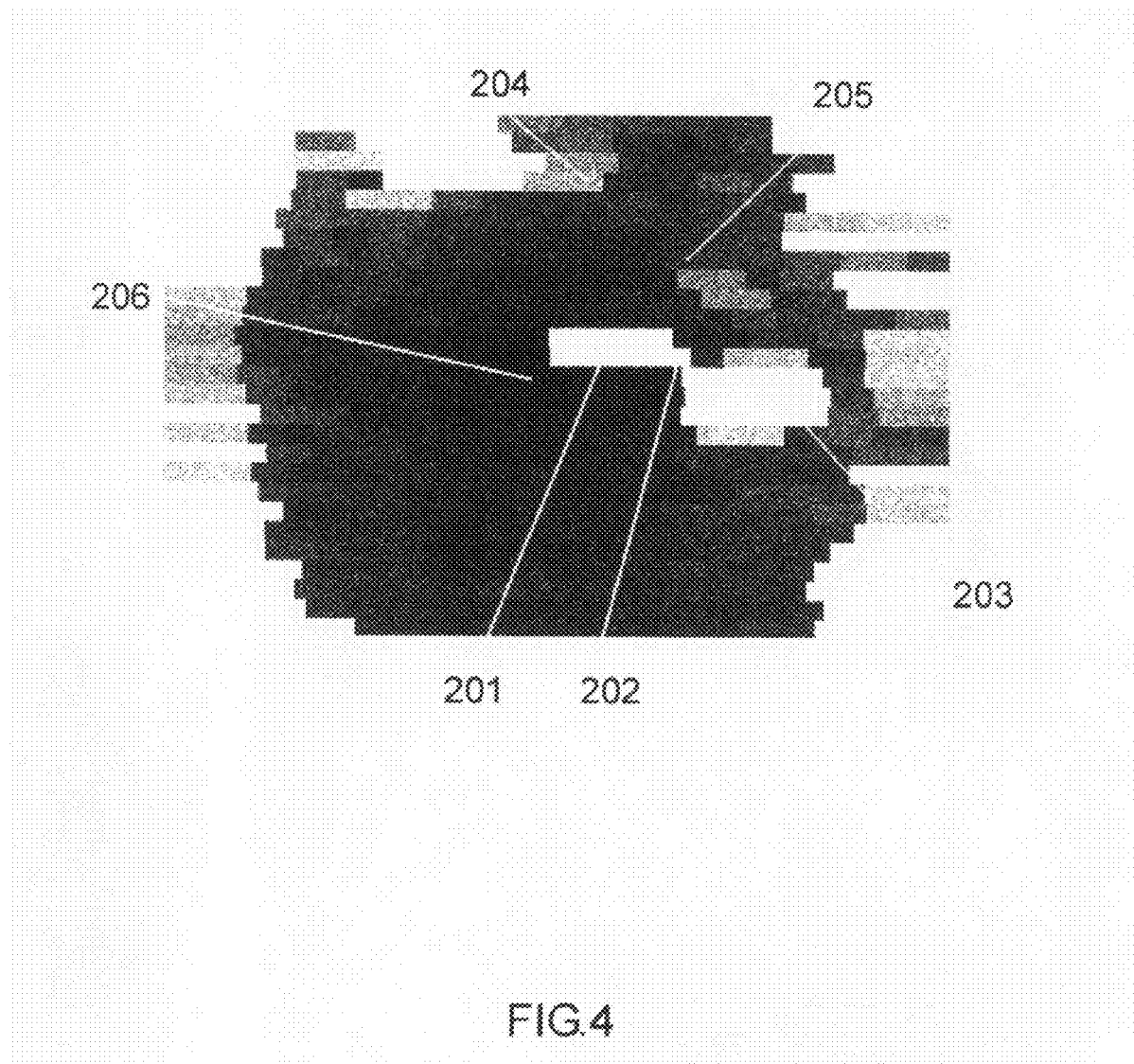
FIG. 4 is an image demonstrating an embodiment of the visual field mapping image generated by a preferred scanning of the present invention of the kinetic perimeter.

FIG. 1, FIG. 2, and FIG. 3 show an embodiment of the scanning, operation, and visual field mapping aspect of the present invention of the kinetic perimeter.

Figure 7:
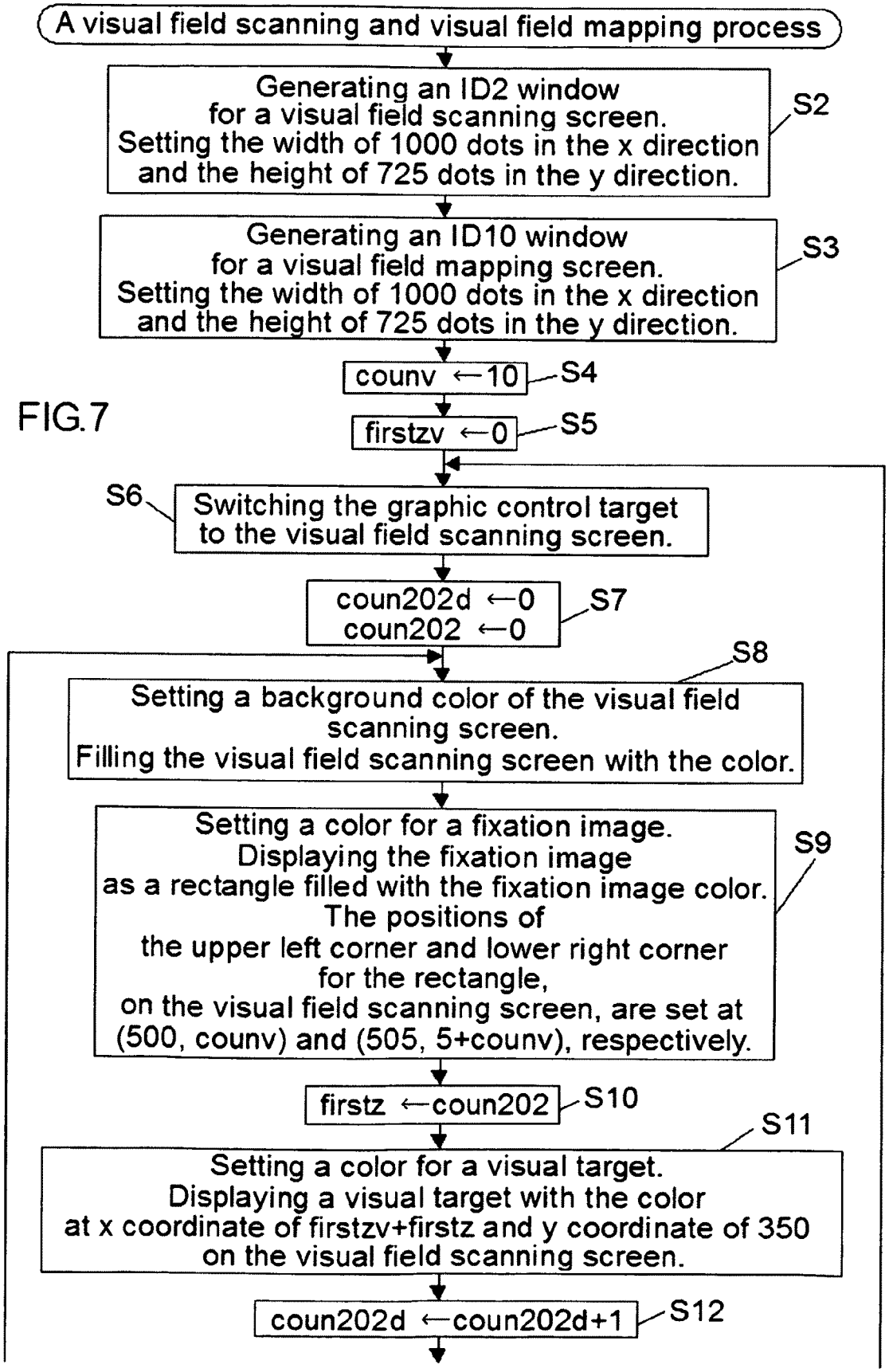
FIG. 7 is a flow chart showing a preferred embodiment of the visual field scanning and visual field mapping process of the present invention of the kinetic perimeter.
Figure 8:
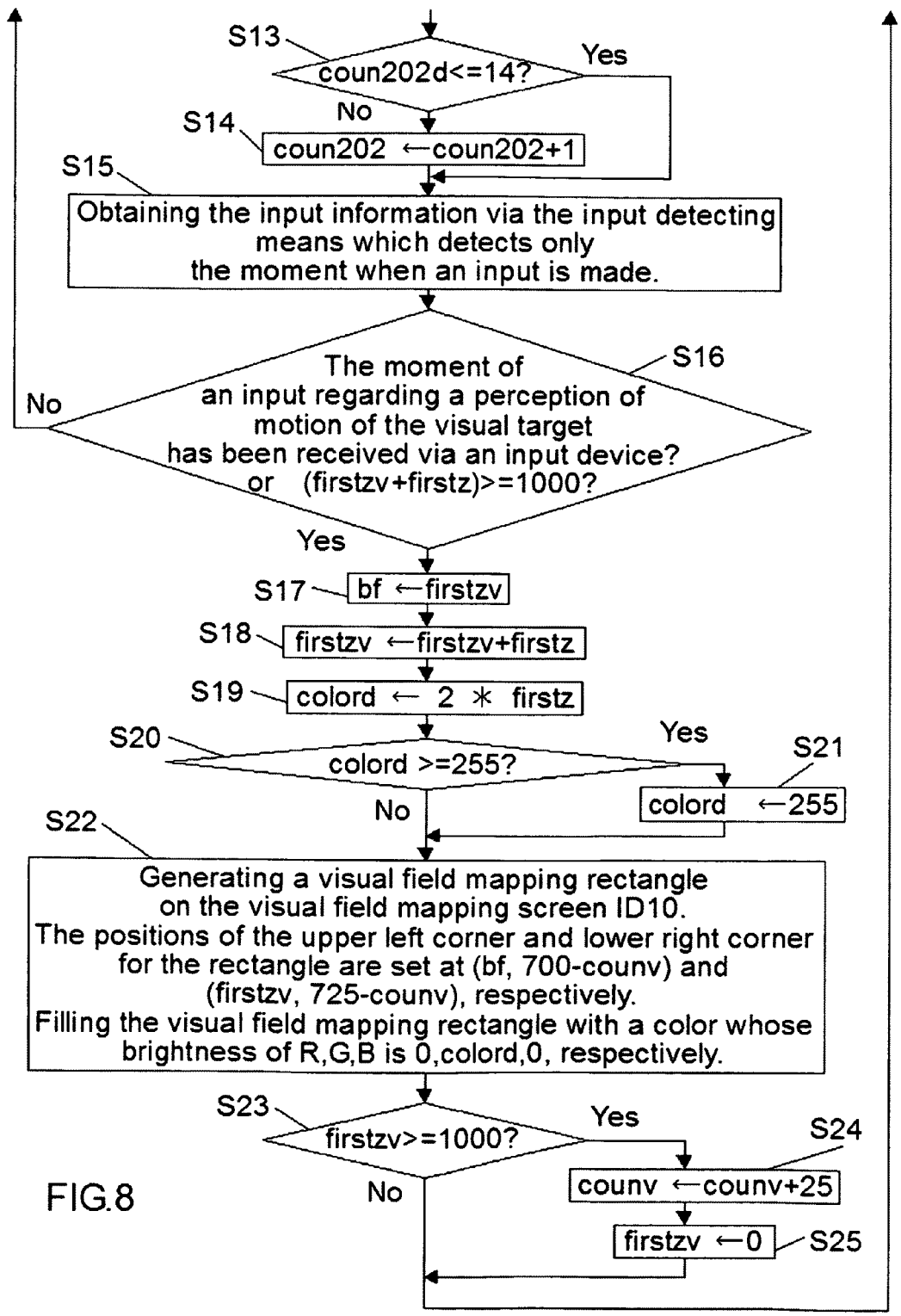
FIG. 8 is a continued flow chart showing a preferred embodiment of the visual field scanning and visual field mapping process of the present invention of the kinetic perimeter.

FIG. 7 and FIG. 8 show an embodiment of the visual field scanning and visual field mapping process of the present invention of the kinetic perimeter.

First, referring to FIG. 1, FIG. 2, and FIG. 3, an embodiment of the scanning, operation, and visual field mapping aspect of the present invention of the kinetic perimeter is described in detail.

A CPU 501 generates a visual field scanning screen 1 on an output device (for example, a display 304).

The CPU 501 sets, in the visual field scanning screen 1, a fixation image scan line 2 according to the program for realizing the present invention of the kinetic perimeter.

The CPU 501 does not display the fixation image scan line 2 on the visual field scanning screen 1, since the fixation image scan line 2 is set as a path for changing the display position of a fixation image with a predetermined spacing, to scan the visual field.

(Although the fixation image scan line 2 is vertically set in FIG. 1, FIG. 2, and FIG. 3, the fixation image scan line 2 may be set with other directionality.)

First, the CPU 501 displays a fixation image 4 at the position of the fixation image 4 on the fixation image scan line 2 in accordance with a program for realizing the present invention of the kinetic perimeter.

The fixation image 4 is to be fixated by an eye of a subject during visual field scanning.

(As will be described below, the CPU 501 changes the display position of the fixation image along the fixation image scan line 2, for example, from the fixation image 4, to a fixation image 5, ..., and to a fixation image 6, etc., to scan the visual field (for example, vertically). The display positions of the fixation image may be, for example, preset on the fixation image scan line 2.)

The CPU 501 sets, in the visual field scanning screen 1, a visual target scan line 3 according to the program for realizing the present invention of the kinetic perimeter.

The CPU 501 does not display the visual target scan line 3 on the visual field scanning screen 1, since the visual target scan line 3 is set as a path of a visual target in the visual field scanning.

(The visual target scan line 3 is set in order to scan the visual field, for example, horizontally.)

(Although the visual target scan line 3 is horizontally set in FIG. 1, FIG. 2, and FIG. 3, the visual target scan line 3 may be set with other directionality.)

The CPU 501 displays first, for example, a visual target 7 statically, at a left side of the visual field scanning screen 1 on the visual target scan line 3, for a predetermined moment in accordance with the program for realizing the present invention of the kinetic perimeter.

And then, the CPU 501 carries out a display control of transforming the visual target 7 into a kinetic visual target and making it move rightward at a predetermined constant velocity.

If an input made when movement of the kinetic visual target has first been perceived by the subject's visual field (more specifically, an input made by a momentary press of, for example, the space key of a keyboard 303) is received through an input device (for example, a keyboard 303 and the like), the CPU 501 displays the kinetic visual target statically at the position at that instant of the kinetic visual target, for example, at the position of a visual target 8, for a predetermined moment (for example, for the same amount of time as the visual target 7 was statically displayed for).

At that time, the CPU 501 stores the display positions of the visual target 7 and the visual target 8, (and if necessary, for example, the distance between the fixation image 4 and the fixation image 5,)(and if necessary, for example, relative locations of the fixation image 4, visual target 7, and visual target 8,) on a memory device (for example, such as a RAM 502, a HDD 504, etc.).

The CPU 501 generates a visual field mapping screen 19 on an output device (for example, the display 304). (The visual field mapping screen 19 may be generated on the output device when the CPU 501 generates the visual field scanning screen 1 on the output device.)

The CPU 501 reads out the display positions of the visual target 7 and visual target 8 (and if necessary, for example, the distance between the fixation image 4 and the fixation image 5,)(and if necessary, for example, relative locations of the fixation image 4, visual target 7, and visual target 8), which are stored on the memory device (for example, such as the RAM 502, the HDD 504, etc.).

The CPU 501 forms and displays a visual field mapping rectangle 20 on the visual field mapping screen 19, based on the readout positions of the visual target 7 and visual target 8 (and if necessary, based, for example, on the distance between the fixation image 4 and the fixation image 5,)(and if necessary, based, for example, on relative locations of the fixation image 4, visual target 7, and visual target 8).

The width of the visual field mapping rectangle 20 is formed based on the display positions of the visual target 7 and the visual target 8, by the CPU 501. The height of the visual field mapping rectangle 20 is formed based, for example, on the distance between the fixation image 4 and the fixation image 5, by the CPU 501.

The display position of the visual field mapping rectangle 20 on the visual field mapping screen 19 is determined based on the display positions of the visual target 7 and visual target 8 (and if necessary, based, for example, on relative locations of the fixation image 4, visual target 7, and visual target 8), by the CPU 501.

The CPU 501 fills the visual field mapping rectangle 20 with, for example, a green (another kind of color may be used for the filling), in accordance with the program for realizing the present invention of the kinetic perimeter.

In the filling, the CPU 501 reads out the distance between the visual target 7 and visual target 8 which is calculated through an arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 20 with a green whose brightness is increased according to length of the distance between the visual target 7 and visual target 8. (The brightness may be set decreasing according to the length of the distance.)

As described above, the CPU 501 displays the visual target 8 statically on the visual field scanning screen 1 for a predetermined moment, and then the CPU 501 carries out a display control of transforming the visual target 8 into a kinetic visual target and making it move rightward at a predetermined constant velocity (for example, at the same velocity as the CPU 501, transforming the statically displayed visual target 7 into the kinetic visual target, made it move on the visual field scanning screen 1 at), in accordance with the program for realizing the present invention of the perimeter.

If an input made when movement of the kinetic visual target has first been perceived by the subject's visual field (more specifically, an input made by a momentary press of, for example, the space key of the keyboard 303) is received through the input device (for example, the keyboard 303 and the like), the CPU 501 displays the kinetic visual target statically at the position at that instant of the kinetic visual target, for example, at the position of a visual target 9, for a predetermined moment (for example, for the same amount of time as the visual target 7 was statically displayed for).

At that time, the CPU 501 stores the display positions of the visual target 8 and the visual target 9 and, for example, the distance between the fixation image 4 and the fixation image 5, (and if necessary, for example, relative locations of the fixation image 4, visual target 8, and visual target 9,) on the memory device (for example, such as the RAM 502, the HDD 504, etc.).

The CPU 501 reads out the display positions of the visual target 8 and visual target 9 (and if necessary, for example, the distance between the fixation image 4 and the fixation image 5,) (and if necessary, for example, relative locations of the fixation image 4, visual target 8, and visual target 9), which are stored on the memory device (for example, such as the RAM 502, the HDD 504, etc.).

The CPU 501 forms and displays a visual field mapping rectangle 21 on the visual field mapping screen 19, based on the readout positions of the visual target 8 and visual target 9, (and if necessary, based, for example, on the distance between the fixation image 4 and the fixation image 5,) (and if necessary, based, for example, on relative locations of the fixation image 4, visual target 8, and visual target 9).

The width of the visual field mapping rectangle 21 is formed based on the display positions of the visual target 8 and the visual target 9, by the CPU 501. The height of the visual field mapping rectangle 21 is formed based, for example, on the distance between the fixation image 4 and the fixation image 5, by the CPU 501.

The display position of the visual field mapping rectangle 21 on the visual field mapping screen 19 is determined based on the display positions of the visual target 8 and visual target 9 (and if necessary, based, for example, on relative locations of the fixation image 4, visual target 8, and visual target 9), by the CPU 501.

The CPU 501 fills the visual field mapping rectangle 21 with, for example, a green (another kind of color may be used for the filling), in accordance with the program for realizing the present invention of the kinetic perimeter.

In the filling, the CPU 501 reads out the distance between the visual target 8 and visual target 9 which is calculated through the arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 21 with a green whose brightness is increased according to length of the distance between the visual target 8 and visual target 9. (The brightness may be set decreasing according to the length of the distance.)

As already described, the CPU 501 displays the visual target 9 statically on the visual field scanning screen 1 for a predetermined moment, and then the CPU 501 carries out a display control of transforming the visual target 9 into a kinetic visual target and making it move rightward at a predetermined constant velocity (for example, at the same velocity as the CPU 501, transforming the statically displayed visual target 7 into the kinetic visual target, made it move on the visual field, scanning screen 1 at), in accordance with the program for realizing the present invention of the kinetic perimeter.

If an input made when movement of the kinetic visual target has first been perceived by the subject's visual field (more specifically, an input made by a momentary press of, for example, the space key of the keyboard 303) is received through the input device (for example, the keyboard 303 and the like), the CPU 501 displays the kinetic visual target statically at the position at that instant of the kinetic visual target, for example, at the position of a visual target 10, for a predetermined moment (for example, for the same amount of time as the visual target 7 was statically displayed for).

At that time, the CPU 501 stores the display positions of the visual target 9 and the visual target 10, (and if necessary, for example, the distance between the fixation image 4 and the fixation image 5,) (and if necessary, for example, relative locations of the fixation image 4, visual target 9, and visual target 10,) on the memory device (for example, such as the RAM 502, the HDD 504, etc.).

The CPU 501 reads out the display positions of the visual target 9 and visual target 10 (and if necessary, for example, the distance between the fixation image 4 and the fixation image 5,) (and if necessary, for example, relative locations of the fixation image 4, visual target 9, and visual target 10), which are stored on the memory device (for example, such as the RAM 502, the HDD 504, etc.).

The CPU 501 forms and displays a visual field mapping rectangle 22 on the visual field mapping screen 19, based on the readout positions of the visual target 9 and visual target 10, (and if necessary, based, for example, on the distance between the fixation image 4 and the fixation image. 5,) (and if necessary, based, for example, on relative locations of the fixation image 4, visual target 9, and visual target 10).

The width of the visual field mapping rectangle 22 is formed based on the display positions of the visual target 9 and the visual target 10, by the CPU 501.

The height of the visual field mapping rectangle 22 is formed based, for example, on the distance between the fixation image 4 and the fixation image 5, by the CPU 501.

The display position of the visual field mapping rectangle 22 on the visual field mapping screen 19 is determined based on the display positions of the visual target 9 and visual target 10 (and if necessary, based, for example, on relative locations of the fixation image 4, visual target 9, and visual target 10), by the CPU 501.

The CPU 501 fills the visual field mapping rectangle 22 with, for example, a green (another kind of color may be used for the filling), in accordance with the program for realizing the present invention of the kinetic perimeter.

In the filling, the CPU 501 reads out the distance between the visual target 9 and visual target 10 which is calculated through the arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 22 with a green whose brightness is increased according to length of the distance between the visual target 9 and visual target 10. (The brightness may be set decreasing according to the length of the distance.)

As already described, the CPU 501 displays the visual target 10 statically on the visual field scanning screen 1 for a predetermined moment, and then the CPU 501 carries out a display control of transforming the visual target 10 into a kinetic visual target and making it move rightward at a predetermined constant velocity (for example, at the same velocity as the CPU 501, transforming the statically displayed visual target 7 into the kinetic visual target, made it move on the visual field scanning screen 1 at), in accordance with the program for realizing the present invention of the kinetic perimeter.

By iterating the similar processing, the CPU 501 is now, for example, supposed to carry out a display control of transforming a visual target 11 into a kinetic visual target and making it move rightward at a predetermined constant velocity (for example, at the same velocity as the CPU 501, transforming the statically displayed visual target 7 into the kinetic visual target, made it move on the visual field scanning screen 1 at), in accordance with the program for realizing the present invention of the kinetic perimeter.

If the kinetic visual target exceeds a right edge on the visual field scanning screen 1, a position 11A, the CPU 501 detects that event through the arithmetic unit and stores a display position of the visual target 11, the position 11A, (and if necessary, for example, the distance between the fixation image 4 and the fixation image 5,) (and if necessary, for example, relative locations of the fixation image 4, the visual target 11, and the position 11A), on the memory device (for example, such as the RAM 502, the HDD 504, etc.).

The CPU 501 reads out the display positions of the visual target 11 and position 11A, (and if necessary, for example, the distance between the fixation image 4 and the fixation image 5,) (and if necessary, for example, relative locations of the fixation image 4, visual target 11, and position 11A), which are stored on the memory device (for example, such as the RAM 502, the HDD 504, etc.).

The CPU 501 forms and displays a visual field mapping rectangle 23 on the visual field mapping screen 19, based on the readout positions of the visual target 11 and position 11A, (and if necessary, based, for example, on the distance between the fixation image 4 and the fixation image 5,) (and if necessary, based, for example, on relative locations of the fixation image 4, visual target 11, and position 11A).

The width of the visual field mapping rectangle 23 is formed based on the display positions of the visual target 11 and the position 11A, by the CPU 501. The height of the visual field mapping rectangle 23 is formed based, for example, on the distance between the fixation image 4 and the fixation image 5, by the CPU 501.

The display position of the visual field mapping rectangle 23 on the visual field mapping screen 19 is determined based on the display positions of the visual target 11 and position 11A (and if necessary, based, for example, on relative locations of the fixation image 4, visual target 11, and position 11A), by the CPU 501.

The CPU 501 fills the visual field mapping rectangle 23 with, for example, a green (another kind of color may be used for the filling), in accordance with the program for realizing the present invention of the kinetic perimeter.

In the filling, the CPU 501 reads out the distance between the visual target 11 and position 11A which is calculated through the arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 23 with a green whose brightness is increased according to length of the distance between the visual target 11 and position 11A. (The brightness may be set decreasing according to the length of the distance.)

As already described, if the visual target, starting rightward kinetic movement from the position of the visual target 11, exceeds the right edge on the visual field scanning screen 1, the position 11A, the CPU 501 detects that event through the arithmetic unit and, in accordance with the program for realizing the present invention of the kinetic perimeter, changes the fixation image display position, on the fixation image scan line 2, from the fixation image 4 to, for example, the fixation image 5 and (if necessary, after waiting a predetermined moment) displays a visual target 12 statically, at a left side of the visual field scanning screen 1 on the visual target scan line 3, for a predetermined moment (for example, for the same amount of time as the visual target 7 was statically displayed for).

And then the CPU 501 carries out a display control of transforming the visual target 12 into a kinetic visual target and making it move rightward at a predetermined constant velocity (for example, at the same velocity as the CPU 501, transforming the statically displayed visual target 7 into the kinetic visual target, made it move on the visual field scanning screen 1 at), in accordance with the program for realizing the present invention of the kinetic perimeter.

If an input made when movement of the kinetic visual target has first been perceived by the subject's visual field (more specifically, an input made by a momentary press of, for example, the space key of the keyboard 303) is received through the input device (for example, the keyboard 303 and the like), the CPU 501 displays the kinetic visual target statically at the position at that instant of the kinetic visual target, for example, at the position of a visual target 13, for a predetermined moment (for example, for the same amount of time as the visual target 7 was statically displayed for).

At that time, the CPU 501 stores the display positions of the visual target 12 and the visual target 13, and, for example, the distance between the fixation image 4 and the fixation image 5 (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it,) (and if necessary, for example, relative locations of the fixation image 5, visual target 12, and visual target 13,) on the memory device (for example, such as the RAM 502, the HDD 504, etc.).

The CPU 501 reads out the display positions of the visual target 12 and visual target 13 and, for example, the distance between the fixation image 4 and the fixation image 5 (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it,) (and if necessary, for example, relative locations of the fixation image 5, visual target 12, and visual target 13), which are stored on the memory device (for example, such as the RAM 502, the HDD 504, etc.).

The CPU 501 forms and displays a visual field mapping rectangle 24 on the visual field mapping screen 19, based on the readout positions of the visual target 12 and visual target 13, and based, for example, on the distance between the fixation image 4 and the fixation image 5 (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it,) (and if necessary, based, for example, on relative locations of the fixation image 5, visual target 12, and visual target 13).

The width of the visual field mapping rectangle 24 is formed based on the display positions of the visual target 12 and the visual target 13, by the CPU 501. The height of the visual field mapping rectangle 24 is formed based, for example, on the distance between the fixation image 4 and the fixation image 5 (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it), by the CPU 501.

The display position of the visual field mapping rectangle 24 on the visual field mapping screen 19 is determined based on the display positions of the visual target 12 and visual target 13 (and if necessary, based, for example, on relative locations of the fixation image 5, visual target 12, and visual target 13), by the CPU 501.

The CPU 501 fills the visual field mapping rectangle 24 with, for example, a green (another kind of color may be used for the filling), in accordance with the program for realizing the present invention of the kinetic perimeter.

In the filling, the CPU 501 reads out the distance between the visual target 12 and visual target 13 which is calculated through the arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 24 with a green whose brightness is increased according to length of the distance between the visual target 12 and visual target 13. (The brightness may be set decreasing according to the length of the distance.)

As already explained, the CPU 501 displays the visual target 13 statically on the visual field scanning screen 1 for a predetermined moment, and then the CPU 501 carries out a display control of transforming the visual target 13 into a kinetic visual target and making it move rightward at a predetermined constant velocity (for example, at the same velocity as the CPU 501, transforming the statically displayed visual target 7 into the kinetic visual target, made it move on the visual field scanning screen 1 at), in accordance with the program for realizing the present invention of the kinetic perimeter.

If an input made when movement of the kinetic visual target has first been perceived by the subject's visual field (more specifically, an input made by a momentary press of, for example, the space key of the keyboard 303) is received through the input device (for example, the keyboard 303 and the like), the CPU 501 displays the kinetic visual target statically at the position at that instant of the kinetic visual target, for example, at the position of a visual target 14, for a predetermined moment (for example, for the same amount of time as the visual target 7 was statically displayed for).

At that time, the CPU 501 stores the display positions of the visual target 13 and the visual target 14, and, for example, the distance between the fixation image 4 and the fixation image 5 (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it), (and if necessary, for example, relative locations of the fixation image 5, visual target 13, and visual target 14,) on the memory device (for example, such as the RAM 502, the HDD 504, etc.).

The CPU 501 reads out the display positions of the visual target 13 and visual target 14 and, for example, the distance between the fixation image 4 and the fixation image 5 (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it,) (and if necessary, for example, relative locations of the fixation image 5, visual target 13, and visual target 14), which are stored on the memory device (for example, such as the RAM 502, the HDD 504, etc.).

The CPU 501 forms and displays a visual field mapping rectangle 25 on the visual field mapping screen 19, based on the readout positions of the visual target 13 and visual target 14, and based, for example, on the distance between the fixation image 4 and the fixation image 5 (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it,) (and if necessary, based, for example, on relative locations of the fixation image 5, visual target 13, and visual target 14).

The width of the visual field mapping rectangle 25 is formed based on the display positions of the visual target 13 and the visual target 14, by the CPU 501. The height of the visual field mapping rectangle 25 is formed based, for example, on the distance between the fixation image 4 and the fixation image 5 (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it), by the CPU 501.

The display position of the visual field mapping rectangle 25 on the visual field mapping screen 19 is determined based on the display positions of the visual target 13 and visual target 14 (and if necessary, based, for example, on relative locations of the fixation image 5, visual target 13, and visual target 14), by the CPU 501.

The CPU 501 fills the visual field mapping rectangle 25 with, for example, a green (another kind of color may be used for the filling), in accordance with the program for realizing the present invention of the kinetic perimeter.

In the filling, the CPU 501 reads out the distance between the visual target 13 and visual target 14 which is calculated through the arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 25 with a green whose brightness is increased according to length of the distance between the visual target 13 and visual target 14. (The brightness may be set decreasing according to the length of the distance.)

As already explained, the CPU 501 displays the visual target 14 statically on the visual field scanning screen 1 for a predetermined moment, and then the CPU 501 carries out a display control of transforming the visual target 14 into a kinetic visual target and making it move rightward at a predetermined constant velocity (for example, at the same velocity as the CPU 501, transforming the statically displayed visual target 7 into the kinetic visual target, made it move on the visual field scanning screen 1 at), in accordance with the program for realizing the present invention of the kinetic perimeter.

If an input made when movement of the kinetic visual target has first been perceived by the subject's visual field (more specifically, an input made by a momentary press of, for example, the space key of the keyboard 303) is received through the input device (for example, the keyboard 303 and the like), the CPU 501 displays the kinetic visual target statically at the position at that instant of the kinetic visual target, for example, at the position of a visual target 15, for a predetermined moment (for example, for the same amount of time as the visual target 7 was statically displayed for).

At that time, the CPU 501 stores the display positions of the visual target 14 and the visual target 15, and, for example, the distance between the fixation image 4 and the fixation image 5 (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it), (and if necessary, for example, relative locations of the fixation image 5, visual target 14, and visual target 15,) on the memory device (for example, such as the RAM 502, the HDD 504, etc.).

The CPU 501 reads out the display positions of the visual target 14 and visual target 15 and, for example, the distance between the fixation image 4 and the fixation image 5 (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it,) (and if necessary, for example, relative locations of the fixation image 5, visual target 14, and visual target 15), which are stored on the memory device (for example, such as the RAM 502, the HDD 504, etc.).

The CPU 501 forms and displays a visual field mapping rectangle 26 on the visual field mapping screen 19, based on the readout positions of the visual target 14 and visual target 15, and based, for example, on the distance between the fixation image 4 and the fixation image 5 (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it,) (and if necessary, based, for example, on relative locations of the fixation image 5, visual target 14, and visual target 15).

The width of the visual field mapping rectangle 26 is formed based on the display positions of the visual target 14 and the visual target 15, by the CPU 501. The height of the visual field mapping rectangle 26 is formed based, for example, on the distance between the fixation image 4 and the fixation image 5 (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it), by the CPU 501.

The display position of the visual field mapping rectangle 26 on the visual field mapping screen 19 is determined based on the display positions of the visual target 14 and visual target 15 (and if necessary, based, for example, on relative locations of the fixation image 5, visual target 14, and visual target 15), by the CPU 501.

The CPU 501 fills the visual field mapping rectangle 26 with, for example, a green (another kind of color may be used for the filling), in accordance with the program for realizing the present invention of the kinetic perimeter.

In the filling, the CPU 501 reads out the distance between the visual target 14 and visual target 15 which is calculated through the arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 26 with a green whose brightness is increased according to length of the distance between the visual target 14 and visual target 15. (The brightness may be set decreasing according to the length of the distance.)

As already explained, the CPU 501 displays the visual target 15 statically on the visual field scanning screen 1 for a predetermined moment, and then the CPU 501 carries out a display control of transforming the visual target 15 into a kinetic visual target and making it move rightward at a predetermined constant velocity (for example, at the same velocity as the CPU 501, transforming the statically displayed visual target 7 into the kinetic visual target, made it move on the visual field scanning screen 1 at), in accordance with the program for realizing the present invention of the kinetic, perimeter.

By iterating the similar processing, the CPU 501 is now, for example, supposed to carry out a display control of transforming the visual target 16 into a kinetic visual target and making it move rightward at a predetermined constant velocity (for example, at the same velocity as the CPU 501, transforming the statically displayed visual target 7 into the kinetic visual target, made it move on the visual field scanning screen 1 at), in accordance with the program for realizing the present invention of the kinetic perimeter.

If the kinetic visual target exceeds a right edge on the visual field scanning screen 1, a position 11A, the CPU 501 detects that event through the arithmetic unit and stores a display position of the visual target 16, the position 11A, (and if necessary, for example, the distance between the fixation image 4 and the fixation image 5,) (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it,) (and if necessary, for example, relative locations of the fixation image 5, the visual target 16, and the position 11A), on the memory device (for example, such as the RAM 502, the HDD 504, etc.).

The CPU 501 reads out the display positions of the visual target 16 and position 11A, and if necessary, for example, the distance between the fixation image 4 and the fixation image 5 (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it,) (and if necessary, for example, relative locations of the fixation image 5, visual target 16, and position 11A), which are stored on the memory device (for example, such as the RAM 502, the HDD 504, etc.).

The CPU 501 forms and displays a visual field mapping rectangle 27 on the visual field mapping screen 19, based on the readout positions of the visual target 16 and position 11A, and if necessary, for example, the distance between the fixation image 4 and the fixation image 5 (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it,) (and if necessary, based, for example, on relative locations of the fixation image 5, visual target 16, and position 11A).

The width of the visual field mapping rectangle 27 is formed based on the display positions of the visual target 16 and the position 11A, by the CPU 501. The height of the visual field mapping rectangle 27 is formed based, for example, on the distance between the fixation image 4 and the fixation image 5 (that is, for example, a distance between the fixation image currently being displayed and gazed at, and its adjacent fixation image already displayed and gazed at and currently erased), (or, for example, a distance based on the distance between the fixation image currently displayed and gazed at, and the fixation image set on the fixation image scan line 2 adjacent to it), by the CPU 501.

The display position of the visual field mapping rectangle 27 on the visual field mapping screen 19 is determined based on the display positions of the visual target 16 and position 11A (and if necessary, based, for example, on relative locations of the fixation image 5, visual target 16, and position 11A), by the CPU 501.

The CPU 501 fills the visual field mapping rectangle 27 with, for example, a green (another kind of color may be used for the filling), in accordance with the program for realizing the present invention of the kinetic perimeter.

In the filling, the CPU 501 reads out the distance between the visual target 16 and position 11A which is calculated through the arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 27 with a green whose brightness is increased according to length of the distance between the visual target 16 and position 11A. (The brightness may be set decreasing according to the length of the distance.)

By iterating the similar processing, the CPU 501 is now, for example, supposed to carry out, under the condition of the fixation image 6 being displayed, a display control of transforming the visual target 17 into a kinetic visual target and making it move rightward at a predetermined constant velocity (for example, at the same velocity as the CPU 501, transforming the statically displayed visual target 7 into the kinetic visual target, made it move on the visual field scanning screen 1 at), in accordance with the program for realizing the present invention of the kinetic perimeter.

If the kinetic visual target exceeds a right edge on the visual field scanning screen 1, a position 11A, the CPU 501 detects that event through the arithmetic unit and stores a display position of the visual target 17, the position 11A, and, for example, the distance between the fixation image 6 currently being displayed and gazed at, and its adjacent fixation image already displayed and gazed at and currently erased, (or, for example, a distance based on the distance between the fixation image currently displayed and gazed at, and the fixation image set on the fixation image scan line 2 adjacent to it,) (and if necessary, for example, relative locations of the fixation image 6, the visual target 17, and the position 11A), on the memory device (for example, such as the RAM 502, the HDD 504, etc.).

The CPU 501 reads out the display positions of the visual target 17 and position 11A, and, for example, the distance between the fixation image 6 currently being displayed and gazed at, and its adjacent fixation image already displayed and gazed at and currently erased, (or, for example, a distance based on the distance between the fixation image currently displayed and gazed at, and the fixation image set on the fixation image scan line 2 adjacent to it,) (and if necessary, for example, relative locations of the fixation image 6, visual target 17, and position 11A), which are stored on the memory device (for example, such as the RAM 502, the HDD 504, etc.).

The CPU 501 forms and displays a visual field mapping rectangle 28 on the visual field mapping screen 19, based on the readout positions of the visual target 17 and position 11A, and, for example, the distance between the fixation image 6 currently being displayed and gazed at, and its adjacent fixation image already displayed and gazed at and currently erased, (or, for example, a distance based on the distance between the fixation image currently displayed and gazed at, and the fixation image set on the fixation image scan line 2 adjacent to it,) (and if necessary, based, for example, on relative locations of the fixation image 6, visual target 17, and position 11A).

The width of the visual field mapping rectangle 28 is formed based on the display positions of the visual target 17 and the position 11A, by the CPU 501. The height of the visual field mapping rectangle 28 is formed based, for example, on the distance between the fixation image 6 currently being displayed and gazed at, and its adjacent fixation image already displayed and gazed at and currently erased (or, for example, a distance based on the distance between the fixation image currently displayed and gazed at, and the fixation image set on the fixation image scan line 2 adjacent to it), by the CPU 501.

The display position of the visual field mapping rectangle 28 on the visual field mapping screen 19 is determined based on the display positions of the visual target 17 and position 11A (and if necessary, based, for example, on relative locations of the fixation image 6, visual target 17, and position 11A), by the CPU 501.

The CPU 501 fills the visual field mapping rectangle 28 with, for example, a green (another kind of color may be used for the filling), in accordance with the program for realizing the present invention of the kinetic perimeter.

In the filling, the CPU 501 reads out the distance between the visual target 17 and position 11A which is calculated through the arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 28 with a green whose brightness is increased according to length of the distance between the visual target 17 and position 11A. (The brightness may be set decreasing according to the length of the distance.)

(In order to clarify the positions of the scotoma 201 and blind spot 203 shown in the visual field mapping screen 19 in relation to the display position of the fixation image on the visual field scanning screen 1, the position on the visual field mapping screen 19, which corresponds to the display position of the fixation image on the visual field scanning screen 1, may be explicitly shown in the visual field mapping screen 19.)

A cluster of visual field mapping rectangles 18, which is to be generated as a result of a visual field scanning, is shown as a reference to the precise positional representation in the visual field scanning screen 1.

A cluster of visual field mapping rectangles 29, which is to be generated as a result of a visual field scanning, is shown as a reference to the precise positional representation in the visual field mapping screen 19.

Regarding a visual field scanning and visual field mapping process carried out by the CPU 501 in accordance with a program for realizing the present invention of the perimeter, the detailed explanation will be disclosed as below while referring to FIG. 7 and FIG. 8.

FIG. 7 and FIG. 8 are flow charts showing a visual field scanning and visual field mapping process to be carried out by a computer shown in FIG. 6.

At the step of S2 of the visual field scanning and visual field mapping process, a CPU 501 generates an ID2 window for a visual field scanning screen 1, on an output device (for example, a display 304).

The CPU 501 sets its width of 1000 dots in the x direction and its height of 725 dots in the y direction.

Hereinafter, the positions are described, in explanation of the visual field scanning screen 1, assuming that the position of the upper left corner of the visual field scanning screen 1 shall be at x coordinate of 0 dot and y coordinate of 0 dot and that an x coordinate axis shall be generated rightward from the upper left corner of the visual field scanning screen 1 and a y coordinate axis shall be generated downward from the upper left corner of the visual field scanning screen 1.

At the step of S3, the CPU 501 generates an ID10 window for a visual field mapping screen 19, on an output device (for example, a display 304).

The CPU 501 sets its width of 1000 dots in the x direction and its height of 725 dots in the y direction.

Hereinafter, in the explanation of the visual field mapping screen 19, positions are described assuming that the position of the upper left corner of the visual field mapping screen 19 shall be at x coordinate of 0 dot and y coordinate of 0 dot and that an x coordinate axis shall be generated rightward from the upper left corner of the visual field mapping screen 19 and a y coordinate axis shall be generated downward from the upper left corner of the visual field mapping screen 19.

At the step of S4, the CPU 501 substitutes, for example, 10 into a variable counv, which is stored on a memory device (for example, such as a RAM 502, a HDD 504, etc.). (The CPU 501 sets the initial value of the variable counv at, for example, 10.)

(For example, a variable counv is associated with the position in the y direction of a fixation target.)

(By initializing the value of the variable counv at 10, the position of a fixation image in the y direction is set at an initial position.)

(A variable counv is associated with, for example, the positions in the y direction of a visual field mapping rectangle 20, a visual field mapping rectangle 21, a visual field mapping rectangle 22, a visual field mapping rectangle 23, a visual field mapping rectangle 24, a visual field mapping rectangle 25, a visual field mapping rectangle 26, a visual field mapping rectangle 27, and a visual field mapping rectangle 28, for example.)

(By initializing the value of the variable counv at 10, the formation position in the y direction of each of visual field mapping rectangles 20, 21, 22, and 23 is set at an initial formation position in the y direction.)

(Forming a part of a fixation image scan line setting means.)
(Forming a part of a fixation image displaying and controlling means.)
(Forming a part of a visual field mapping means.)
(Forming a part of a visual field mapping rectangle forming means.)

At the step of S5, the CPU 501 initializes the value of a variable firstzv at, for example, 0.
(Relating to the setting of the initial display position (for example, in the x direction) of a visual target displayed on the visual field scanning screen 1.)
(Forming a part of a visual target scan line setting means.)
(Forming a part of a visual target displaying and controlling means.)
(Forming a part of a static display position storing means.)

At the step of S6, the CPU 501 switches the graphic control target to the visual field scanning screen 1.

At the step of S7, the CPU 501 initializes the value of a variable coun202d at, for example, 0.

At the step of S7, the CPU 501 initializes the value of a variable coun202 (the variable coun202 being the variable to be used in displaying and controlling a visual target kinetically as at S14) at, for example, 0.

(Relating to the setting of the initial display position (for example, in the x direction) of a visual target displayed on the visual field scanning screen 1.)

(Forming a part of a statically displaying and controlling means.)

(Forming a part of a under the same fixation image scanning continuation means.)

(Forming a part of a scanning switching means to the scanning under the next fixation image.)

At the step of S8, the CPU 501 sets a background color of the visual field scanning screen 1, and fills the visual field scanning screen 1 with the color.

(Forming a part of a fixation image displaying and controlling means.)

(Forming a part of a visual target displaying and controlling means.)

At the step of S9, the CPU 501 sets a color for a fixation image, and displays (in the present invention, for example,) a rectangle (i.e., a fixation image) filled with the fixation image color, on the visual field scanning screen 1.

The positions of the upper left corner and lower right corner for the rectangle on the visual field scanning screen 1 are set at, for example, (500, counv) and (505, 5+counv), respectively. (Unit of dot.)

(Forming a part of a fixation image scan line setting means.)

(Forming a part of a fixation image displaying and controlling means.)

At the step of S10, the CPU 501 substitutes the value of the variable coun202 into a variable firstz stored on a memory device (for example, such as a RAM 502, a HDD 504, etc.).

(The variable firstz is a distance storing means. (but if a visual target exceeds a right edge of the visual field scanning screen 1 and (firstzv+firstz)>=1000 is satisfied, a distance from the position of the right edge of the visual field scanning screen 1 to a starting position of the kinetic display control of the visual target just before its reaching the right edge, may be set to be stored in a variable firstz, as at S16 and S19.))

(And a value stored in a variable firstz is the value representing the length in width of a visual field mapping rectangle generated at S22, and converted, by the arithmetic unit at S19 and S20, into a numeric value for designating a color with which the visual field mapping rectangle is filled.)

(If necessary, a color other than above mentioned may be designated for visual field mapping rectangles adjacently generated to both ends of a scan line.)

(Forming a part of a visual target scan line setting means.)

(Forming a part of a kinetic display and control starting means.)

(Forming a part of a distance storing means.)

(Forming a part of a visual field mapping means.)

(Forming a part of a visual field mapping rectangle image processing means.)

At the step of S11, the CPU 501 sets the display aspects for a visual target, such as a color, size, and shape.

The CPU 501, carrying out a computation through an arithmetic unit, displays the visual target with the display aspects (the visual target color, etc.), for example, at x coordinate of firstzv+firstz dots and y coordinate of, (in the present invention, for example,) 350 dots on the visual field scanning screen 1.

(Forming a part of a visual target scan line setting means.)

(Forming a part of a visual target displaying and controlling means.)

At the step of S12, the CPU 501 increments the value of the variable coun202d by, for example, one and stores the result on a memory device (for example, such as a RAM 502, a HDD 504, etc.).

(Forming a part of a statically displaying and controlling means.)

(Forming a part of a kinetic display and control starting means.)

At the step of S13, the CPU 501 makes a judgement whether coun202d<=14, through an arithmetic unit.

(Although the "14" in "coun202d<=14" are the value relating to the setting of a predetermined moment during which a visual target is displayed statically by the statically displaying and controlling means, another value may be used for the setting.)

At the step of S13, the CPU 501 moves to S15 and continues the processing if the CPU 501 judges that coun202d<=14 holds.

(Forming a part of a statically displaying and controlling means.)

(S7, S12, and S13 are examples of the preferred embodiments of the present invention of the setting of the predetermined moment, (during which a visual target is statically displayed by the statically displaying and controlling means).)

At the step of S13, the CPU 501 moves to S14 and continues the processing if the CPU 501 judges that coun202d<=14 does not hold.

(Forming a part of a kinetic display and control starting means.)

At the step of S14, the CPU 501, through an arithmetic unit, increments the value of coun202 by, for example, one and stores the result on a memory device (for example, such as a RAM 502, a HDD 504, etc.).

Such an increment is set so as to cause a visual target to take on a kinetic characteristic (the value of the increment may be set by another value).

(Forming a part of a kinetic display and control starting means.)

At the step of S15, the CPU 501 obtains input information to detect (for example) only the moment when an input (made, via an input device (for example, a keyboard 303 and the like), regarding the perception of visual target movement) is made.

(Forming a part of a detecting means.)

(Detecting only the moment when an input is made is such a detection as detects the information on the press only once per the depression of, for example, the space key (for example, for a keyboard 303) and after that leaves the depression undetected until the depressed space key is released. (The detection of an input via the detecting means may not be limited to such a moment.))

At the step of S16, a judgement on if "the moment of an input regarding a perception of motion of the visual target has been received via an input device (for example, a keyboard 303 and the like)" or "(firstzv+firstz)>=1000 is satisfied", is made by the CPU 501.

If neither holds, the CPU 501 goes back to S8 and continues carrying out the process.

(Forming a part of a visual target displaying and controlling means.)

(Forming a part of a detecting means.)

In the judgement at the step of S16 on if "the moment of an input regarding a perception of motion of the visual target has been received via an input device (for example, a keyboard 303 and the like)" or "(firstzv+firstz)>=1000 is satisfied", when the CPU 501 judges that either or both hold, the CPU 501 moves on to S17.
(Forming a part of a detecting means.)
(Forming a part of a under the same fixation image scanning continuation means.)
(Forming a part of a scanning switching means to the scanning under the next fixation image.)
At the step of S17, the CPU 501 substitutes the value of a variable firstzv into the variable bf, and stores that value on a memory device (for example, such as a RAM 502, a HDD 504, etc.).
(Forming a part of a static display position storing means.)
(Forming a part of a visual field mapping means.)
(Forming a part of a visual field mapping rectangle forming means.)
(At the step of S22, a variable bf is a part of a visual field mapping rectangle forming means, equaling to the x coordinate of a left side of a visual field mapping rectangle (for example, each of visual field mapping rectangles 20, 21, 22, 23, 24, 25, 26, 27, and 28) generated at S22.)
At the step of S18, the CPU 501 substitutes the value of (firstzv+firstz) computed via an arithmetic unit into a variable firstzv stored on a memory device (for example, such as a RAM 502, a HDD 504, etc.).
(Forming a part of a detecting means.)
(Forming a part of a visual field mapping means.)
(Forming a part of a visual field mapping rectangle forming means.)
(Forming a part of a under the same fixation image scanning continuation means.)
(If a visual target exceeds a right edge of the visual field scanning screen 1 and (firstzv+firstz)>=1000 is satisfied, the detection position storing means may store, in a variable firstzv, the x coordinate of the right edge of the visual field scanning screen 1 in substitution for a position of a visual target at the time of the detection by a detecting means, as at S16 and S22.)
(At S22, the variable firstzv forms a part of a visual field mapping rectangle forming means, equaling to the x coordinate of a right side of a visual field mapping rectangle (for example, each of visual field mapping rectangles 20, 21, 22, 23, 24, 25, 26, 27, and 28) generated at S22.)
At the step of S19, the CPU 501 reads out the value of the variable firstz stored on a memory device (for example, such as a. RAM 502, a HDD 504, etc.) and carries out a computation of 2* firstz through an arithmetic unit, substituting the result into a variable colord, which is stored on a memory device (for example, such as a RAM 502, a HDD 504, etc.).
(Forming a part of a visual field mapping means.)
(Forming a part of a visual field mapping rectangle image processing means.)
At the step of S20, the value of a variable colord stored on the memory device (for example, such as the RAM 502, the HDD 504, etc.) is read out by the CPU 501, and a judgement whether colord>=255, is made through an arithmetic unit by the CPU 501.
At the step of S20, the CPU 501 moves to S22 and continues the processing if the CPU 501 judges that colord>=255 does not hold.
(Forming a part of a visual field mapping means.)
(Forming a part of a visual field mapping rectangle image processing means.)
When at the step of S20 the CPU 501 judges that colord>=255 holds, the CPU 501 updates, at S21, the value of colord with 255, stores that value in a memory device (for example, such as a RAM 502, a HDD 504, etc.), and moves on to S22, continuing the processing.
(Forming a part of a visual field mapping means.)
(Forming a part of a visual field mapping rectangle image processing means.)
At the step of S22, the CPU 501 generates a visual field mapping rectangle (for example, any one of visual field mapping rectangles 20, 21, 22, 23, 24, 25, 26, 27, and 28) on the visual field mapping screen 19.
The CPU 501 sets the position of the upper left point of the rectangle (for example, the one of visual field mapping rectangles 20, 21, 22, 23, 24, 25, 26, 27, and 28) at (bf, 700−counv), and sets the position of the lower right point of the rectangle at (firstzv, 725−counv) (unit of dot).
(Forming a part of a visual field mapping means.)
(Forming a part of a visual field mapping rectangle forming means.)
The CPU 501 fills the visual field mapping rectangle with a color whose brightness of R,G,B is, for example, 0,colord,0, respectively.
(Forming a part of a visual field mapping means.)
(Forming a part of a visual field mapping rectangle image processing means.)
At the step of S23, the CPU 501 judges, via an arithmetic unit, whether firstzv>=1000.
If the CPU 501 judges, at S23, that firstzv>=1000 does not hold, the CPU 501 goes back to S6, continuing the processing.
(Forming a part of a under the same fixation image scanning continuation means.)
If the CPU 501 judges, at S23, that firstzv>=1000 is satisfied, the CPU 501 increments, at S24, the value of a variable counv by, for example, 25 (another value may be used), which is stored on a memory device (for example, such as a RAM 502, a HDD 504, etc.), and then the CPU 501 moves on to S25, continuing the processing.
(Forming a part of a fixation image scan line setting means.)
(Forming a part of a fixation image displaying and controlling means.)
(Forming a part of a visual field mapping means.)
(Forming a part of a visual field mapping rectangle forming means.)
(Forming a part of a scanning switching means to the scanning under the next fixation image.)
At the step of S25, the CPU 501 initializes the value of a variable firstzv at, for example, zero, which is stored on a memory device, and then the CPU 501 goes back to S6, continuing the processing.
(Forming a part of a scanning switching means to the scanning under the next fixation image.)
(Forming a part of a visual target scan line setting means.)
(Forming a part of a visual target displaying and controlling means.)
(Forming a part of a static display position storing means.)

What is claimed is:
1. An operational method for a kinetic perimeter comprising:
　a step of visual field scanning screen generating means for generating, on an output device, a visual field scanning screen for scanning a visual field of a subject;
　a step of fixation image scan line setting means for setting a fixation image scan line and a fixation image display position, for carrying out the scanning of changing the display position of a fixation image with a predetermined spacing, on the visual field scanning screen that is generated, on the output device, by said step of visual field scanning screen generating means;

a step of fixation image displaying and controlling means for displaying and controlling a fixation image to be fixated by the subject, during a visual field scanning, at a fixation image display position on the fixation image scan line which is set by said step of fixation image scan line setting means;

a step of visual target scan line orthogonally setting means for setting a visual target scan line normal to said fixation image scan line, to scan a visual target on said visual field scanning screen;

a step of visual target displaying and controlling means for displaying and scanning said visual target on said visual field scanning screen along the visual target scan line set by said step of visual target scan line orthogonally setting means, in order to scan the visual field;

a step of statically displaying and controlling means, which is comprised in said step of visual target displaying and controlling means, for statically displaying and controlling said visual target for a predetermined moment on said visual target scan line;

a step of static display position storing means for storing, on a memory device, a position of said visual target statically displayed and controlled for said predetermined moment by said step of statically displaying and controlling means;

a step of kinetic display and control starting means, which is comprised in said step of visual target displaying and controlling means, for starting a kinetic scan of said visual target along said visual target scan line after said step of statically displaying and controlling means has displayed and controlled said visual target statically for said predetermined moment;

a step of detecting means for, via an input device, detecting a time when said kinetic scan, started by said step of kinetic display and control starting means, of said visual target has first been perceived by the subject's visual field;

a step of detection position storing means for storing, on the memory device, a position of said visual target at the time of the detection by said step of detecting means;

a step of visual field mapping screen generating means for generating a visual field mapping screen, on an output device, to map and display the subject's visual field;

a step of visual field mapping means for carrying out a visual field mapping on said visual field mapping screen, referring to a position of said visual target stored by said step of static display position storing means and a position of said visual target stored by said step of detection position storing means;

a step of kinetic scan stopping means for stopping, through said step of visual target displaying and controlling means, said kinetic scan of said step of kinetic display and control starting means if the time when said kinetic scan has first been perceived by the subject's visual field is detected by said step of detecting means;

a step of under the same fixation image scanning continuation means for, by said step of visual target displaying and controlling means through said step of statically displaying and controlling means, displaying and controlling said visual target statically for said predetermined moment, on said visual target scan line at the position of said visual target stored by said step of detection position storing means, and proceeding from said step of static display position storing means onward as above, and continuing the similar scan, under said fixation image displayed, of said visual target scan line by iterating above procedure along said visual target scan line under the condition of said fixation image being displayed by said step of fixation image displaying and controlling means, in order to continue the next scan of said visual target scan line;

and a step of scanning switching means, to the scanning under the next fixation image, for, if the scan, under said fixation image, of said visual target scan line is completed by said step of under the same fixation image scanning continuation means, continuing the similar scan, under a next fixation image being displayed, of said visual target scan line by said step of visual target displaying and controlling means with the next fixation image being said fixation image whose display position is changed, by said step of fixation image displaying and controlling means, to a position with said predetermined spacing, along the fixation image scan line set by said fixation image scan line setting means.

2. A computer-readable non-transitory medium recording a program for causing a computer to realize a function comprising:

visual field scanning screen generating means for generating, on an output device, a visual field scanning screen for scanning a visual field of a subject;

fixation image scan line setting means for setting a fixation image scan line and a fixation image display position, for carrying out the scanning of changing the display position of a fixation image with a predetermined spacing, on the visual field scanning screen that is generated, on the output device, by said visual field scanning screen generating means;

fixation image displaying and controlling means for displaying and controlling a fixation image to be fixated by the subject, during a visual field scanning, at a fixation image display position on the fixation image scan line which is set by said fixation image scan line setting means;

visual target scan line orthogonally setting means for setting a visual target scan line normal to said fixation image scan line, to scan a visual target on said visual field scanning screen;

visual target displaying and controlling means for displaying and scanning said visual target on said visual field scanning screen along the visual target scan line set by said visual target scan line orthogonally setting means, in order to scan the visual field;

statically displaying and controlling means, which is comprised in said visual target displaying and controlling means, for statically displaying and controlling said visual target for a predetermined moment on said visual target scan line;

static display position storing means for storing, on a memory device, a position of said visual target statically displayed and controlled for said predetermined moment by said statically displaying and controlling means;

kinetic display and control starting means, which is comprised in said visual target displaying and controlling means, for starting a kinetic scan of said visual target along said visual target scan line after said statically displaying and controlling means has displayed and controlled said visual target statically for said predetermined moment;

detecting means for, via an input device, detecting a time when said kinetic scan, started by said kinetic display and control starting means, of said visual target has first been perceived by the subject's visual field;

detection position storing means for storing, on the memory device, a position of said visual target at the time of the detection by said detecting means;

visual field mapping screen generating means for generating a visual field mapping screen, on an output device, to map and display the subject's visual field;

visual field mapping means for carrying out a visual field mapping on said visual field mapping screen, referring to a position of said visual target stored by said static display position storing means and a position of said visual target stored by said detection position storing means;

kinetic scan stopping means for stopping, through said visual target displaying and controlling means, said kinetic scan of said kinetic display and control starting means if the time when said kinetic scan has first been perceived by the subject's visual field is detected by said detecting means;

under the same fixation image scanning continuation means for, by said visual target displaying and controlling means through said statically displaying and controlling means, displaying and controlling said visual target statically for said predetermined moment, on said visual target scan line at the position of said visual target stored by said detection position storing means, and proceeding from said static display position storing means onward as above, and continuing the similar scan, under said fixation image displayed, of said visual target scan line by iterating above procedure along said visual target scan line under the condition of said fixation image being displayed by said fixation image displaying and controlling means, in order to continue the next scan of said visual target scan line;

and scanning switching means, to the scanning under the next fixation image, for, if the scan, under said fixation image, of said visual target scan line is completed by said under the same fixation image scanning continuation means, continuing the similar scan, under a next fixation image being displayed, of said visual target scan line by said visual target displaying and controlling means with the next fixation image being said fixation image whose display position is changed, by said fixation image displaying and controlling means, to a position with said predetermined spacing, along the fixation image scan line set by said fixation image scan line setting means.

* * * * *